(12) United States Patent
de Baar et al.

(10) Patent No.: US 6,750,014 B2
(45) Date of Patent: Jun. 15, 2004

(54) REDUCING BACKGROUND IN HYBRIDIZATION REACTIONS

(75) Inventors: Marinus Petrus de Baar, Utrecht (NL); Eveline Catherina A. C. Timmermans, 's-Hertogenbosch (NL); Bob van Gemen, Almere (NL)

(73) Assignee: PrimaGen Holding B.V., Amsterdam (NL)

( * ) Notice: Subject to any disclaimer, the term of this patent is extended or adjusted under 35 U.S.C. 154(b) by 12 days.

(21) Appl. No.: 09/785,881

(22) Filed: Feb. 16, 2001

(65) Prior Publication Data

US 2002/0001802 A1 Jan. 3, 2002

(30) Foreign Application Priority Data

Feb. 17, 2000 (EP) .............................. 00200549

(51) Int. Cl.$^7$ .......................... C12Q 1/68; C12N 15/00; C12N 15/63; C12N 1/20; C07H 21/04
(52) U.S. Cl. ..................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search .......................... 435/6, 91.1, 91.2, 435/91, 803, 810; 536/24.3; 935/6, 9, 78; 436/518, 808, 811

(56) References Cited

U.S. PATENT DOCUMENTS

| 4,683,194 A | * | 7/1987 | Saiki et al. ..................... 435/6 |
| 5,215,899 A | * | 6/1993 | Dattagupta ..................... 435/6 |
| 5,607,834 A | * | 3/1997 | Bagwell ........................ 435/6 |
| 6,027,880 A | * | 2/2000 | Cronin et al. ................... 435/6 |

FOREIGN PATENT DOCUMENTS

WO    WO 96/40902    12/1996

OTHER PUBLICATIONS

Tyagi et al., Wavelength–shifting molecular beacons, Nature Biotechnology, Nov. 2000, pp. 1191–1196, vol. 18.
European Search Report, EP 00 20 0549, dated Jul. 31, 2000, 3 pages.

Guo et al., "Enhanced discrimination of single nucleotide polymorphisms by artificial mismatch hybridization", Nature Biotechnology, vol. 15, pp. 331–335.

Leone et al., "Molecular beacon probes combined with amplification by NASBA enable homogeneous, real–time detection of RNA", Nucleic Acids Research, vol. 26, No. 9, pp. 2150–2155, 1998.

Marras et al., "Multiplex detection of single–nucleotide variations using molecular beacons", Genetic Analysis: Biomolecular Engineering, 14, pp. 151–156, 1999.

Morris et al., "Rapid Reverse Transcription–PCR Detection of Hepatitis C Virus RNA in Serum by Using the TaqMan Fluorogenic Detection System", Journal of Clinical Microbiology, vol. 34, No. 12, pp. 2933–2936, Dec. 1996.

Tyagi et al., "Multicolor molecular beacons for allele discrimination", Nature Biotechnology, vol. 16, pp. 49–53, Jan. 1998.

* cited by examiner

Primary Examiner—Jeffrey Fredman
Assistant Examiner—Arun Chakrabarti
(74) Attorney, Agent, or Firm—TraskBritt

(57) ABSTRACT

The invention provides a method for reducing background in hybridization reactions of nucleic acids involving at least two homologous probes, wherein at least one of the probes is non-linear, or two homologous target sequences and a non-linear probe. Background is reduced by introducing an intended mismatch with a target sequence in at least one of the probes. The presence of the mismatch reduces the specificity of probes not entirely complementary to a target sequence to such an extent that the background signal is reduced. A set of mixed homologous probes, wherein at least one of the probes is non-linear, comprising such specific mismatch is also provided. The set can be used for the detection of variants of a family of nucleic acids, for instance a number of HIV variants. The invention also provides kits for carrying out the methods according to the invention.

17 Claims, 1 Drawing Sheet

REDUCING BACKGROUND IN HYBRIDIZATION REACTIONS

TECHNICAL FIELD

The present invention relates to the field of molecular biology. In particular the invention relates to methods for detecting, identifying and/or distinguishing between nucleic acid molecules or functional analogues thereof, such as PNA's.

BACKGROUND

The most common method for identification of a nucleic acid sequence is the hybridization of a sequence specific short piece of DNA (probe) to the complementary sequence in the target nucleic acid (DNA or RNA). This can then be followed by the extension of the probe through the action of a nucleic acid polymerase or ligase. Usually, the probe is labeled (directly, indirectly; before, during or after hybridization) with a detectable moiety. For instance, a radioactive or fluorescent group can be included to indicate the presence of the (hybridized) probe at a certain position or place. In a typical protocol, the probe-target complex is formed after the hybridization is washed (bound-free separation) to remove non-bound probe. The amount of probe that remains attached to the target, as indicated by the label, is a measure for the amount of target that has a complementary sequence of the probe. When no signal is obtained, the target sequence is absent, or is at least below the detection levels.

This method of probe hybridization is also commonly used for the detection and quantification of nucleic acids belonging to pathogenic microorganisms in clinical samples. In some protocols, the nucleic acid from the microorganism is first amplified with a nucleic acid amplification method such as PCR, NASBA, SDA, TMA or others, before the amplified nucleic acid is detected by probe hybridization. In more recently described methods, the probe hybridization takes place during the generation of the amplified nucleic acid in the amplification reaction itself. In this protocol, the signal of the label attached to the probe becomes detectable only after the probe has hybridized to the complementary nucleic acid. Examples of such probes that enable real-time homogeneous detection in amplification reactions are the TaqMan[1,2] and Molecular Beacon[3,4] probes.

Another feature of probes is the identification of small changes (i.e. mutations) in the nucleotide sequence. Single nucleotide mutations and larger mutations, including insertions and deletions, can be detected by the application of specific probes that are the complement of the sequence encompassing the mutation. Commonly, the probes are short oligonucleotides consisting of approximately 15–50 nucleotides, preferably about 20 nucleotides with a mutated position somewhere in the middle of the sequence. The probe will not be able to hybridize or the probe will hybridize with reduced efficiency in case there is no complete match between the probe and the target sequence. Only a completely matched probe will give a good detectable signal. If multiple probes are used that are specific for different sequences with mutations in the probe, a signal that matched the target and the mutation is identified in the end. There are many variations on this theme, but the basic principle is of two complementary sequences that hybridize when there are no mismatches is always present. This strategy for identifying of single nucleotide mutations is preferably applied to molecular beacon probes[6,7], because non-linear probes have a high specificity.

A problem occurs however, when looking for small variations in target sequences, such as point mutations. When mixed probes are applied, those probes that have only a mismatch at the site of the point mutation will hybridize to the target sequence, competing with the probe that has an exact complementary sequence to the target sequence. Although this binding is weaker than that of the exact fit, it gives rise to background, which may be considered a positive signal and may lead to false positives. The reverse is also true. When there are homologous target sequences present, competition for a single kind of probe may occur. Even in systems where single probes and/or single target sequences per container are used, the results start to overlap and the distinguishing capacity may be insufficient. This occurs when there are large homologies in hybridizing areas which are the same in different containers containing related, but not identical probes and/or target sequences.

BRIEF SUMMARY OF THE INVENTION

We found that the introduction of a mismatch in a non-linear probe, such as a beacon probe, enhances the specificity of the probe in a mixed set of homologous probes for the detection of point mutations in a sequence. We also found that using a single non-linear probe having a mismatch for at least one of a member of a family of target sequences also enhances the specificity by reducing background signals. This result is unexpected, because until the present invention it was stated that introduced mismatches in non-linear probes resulted in very unstable hybrids.[7] It was suggested that a hairpin probe, such as a beacon probe, hardly binds its target sequence anymore after one introduced mismatch. Only linear probes would significantly bind their target sequence after the introduction of a mismatch. Therefore, only linear probes were thought to be suitable for intended introduction of a mismatch to reduce background. However, we have found that hybridization of non-linear probes comprising a mismatch with a target sequence is indeed possible, and that the amount of formed hybrids and the stability of the hybrids is sufficient to perform identification of a nucleic acid sequence. Moreover, the introduction of an intended mismatch in non-linear probes reduces background in hybridization reactions.

Thus, the invention provides a method for reducing background in a hybridization reaction of nucleic acids involving mixed homologous probes, wherein at least one of the probes is non-linear, comprising introducing, a mismatch with an intended target sequence in at least one of the non-linear probes. The presence of the mismatch reduces the specificity of probes not entirely complementary to a target sequence to such an extent that the background signal is at least significantly reduced. This is particularly useful in methods where the probes are very similar, for instance when single point mutations must be detectable. Thus, in a preferred method the invention provides a method in which the probes are designed to detect point mutations in target sequences, and more specifically a method wherein at least two of the probes comprise an identical sequence except for the variation of the point mutation and possibly the site of the mismatch. This does not mean that the sequences must be identical over the whole of the molecule, but that they are identical in the part where hybridization should occur. This is a situation in which false positives are a significant risk. The mismatch should comprise as many nucleotides as necessary to significantly lower the background, but not so many nucleotides that the probe having the exact match for the allelic variation (point mutation) has a significantly lower binding affinity. The number depends of course on the length of the probe and the base composition of the probe. Typically no more than 10 percent of the probe should be mismatch, preferably less than 5%, and especially about 1–3 nucleotides in a 20 nucleotide probe or the corresponding percentage in a shorter or longer probe. Thus, in a further embodiment the invention provides a method wherein the mismatch comprises 1–3 nucleotides. For the same reasons as mentioned above, the mismatch should be located not too close, but also not too far away from the actual site of variation. Typically in a 20 nucleotide probe it should be located between 2 and 5 nucleotides from the site of variation. Thus, in a further embodiment the invention provides a method wherein the mismatch is located between 2 and 20 nucleotides up-or downstream of the point mutation.

Probe length is not really critical. Conventional probe lengths are suitable. Usually probes should not exceed 50 nucleotides and should not be less than 15 nucleotides, with a good average at about 20 nucleotides. Thus, in yet another embodiment the invention provides a method wherein at least one non-linear probe has a length of about 15–50 nucleotides. As stated above, a label is typically applied for detection of bound (sometimes unbound) probe. The label may be any conventional label, and it may be attached to the probe or the hybridized complex at any suitable time. Thus, in yet another embodiment, the invention provides a method wherein at least one of the mixed homologous non-linear probes is provided with a detectable moiety. Before or after the hybridization step, conventional amplification and/or purification steps may be employed in the methods of the invention. All such methods are well known in the art and need no further explanation here. Therefore, the invention further provides a method which includes an amplification step.

Sets of probes designed for the methods of the present invention are also provided by the invention. Thus, the invention provides e.g., a set of mixed homologous probes for detection of at least one allelic variant of a nucleic acid family, wherein at least one of the probes is non-linear, the probes comprise sequences that are completely complementary to and are specific for one of the allelic variants of the family, except for a specific mismatch located upstream and/or downstream from the site of variation.

The invention further provides a set of mixed homologous primers, wherein at least two of the probes comprise an identical sequence except for the variation of a point mutation and possibly the site of the mismatch, preferably a set wherein the mismatch comprises 1–3 nucleotides. The reasons for the design of the sets of primers have been explained above and will become more apparent from the experimental part. The invention also provides a set wherein the mismatch is located 2–20 nucleotides upstream or downstream of the point mutation, whereby the probes typically have lengths between 15 and 50 nucleotides. Furthermore, the invention also provides using the methods and the probes in molecular biology in general, and in the detection of point mutations and allelic variants in particular, especially in the field of detection of pathogens, in particular of HIV variants. Thus, the invention further provides the use of a set of probes according to the invention for the detection of variants of a family of nucleic acids, particularly wherein the family of nucleic acids is derived from a family of pathogens, in particular, wherein the family represents a number of HIV-variants. Kits for carrying out the methods according to the invention are also provided.

DETAILED DESCRIPTION OF THE PREFERRED EMBODIMENTS

Figure 1:
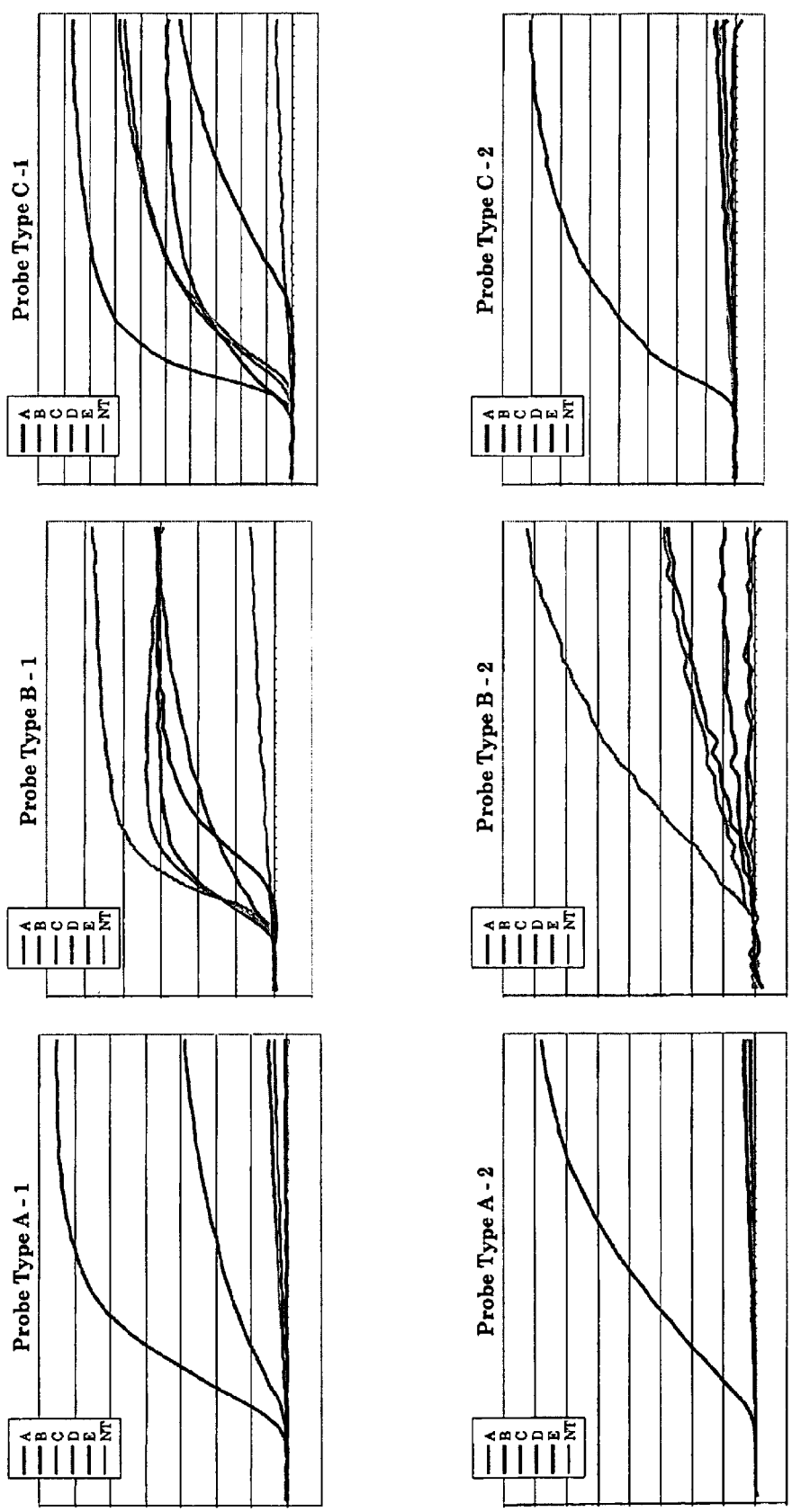
FIG. 1 is a depiction of real time signal generation of NASBA reactions with different molecular beacon probes (see table 1 for details) using different HIV-1 strains as input.

The invention is further explained by the use of the following example. This illustrative example is not to limit the invention in any way.

EXAMPLE 1

In this example, nucleic acid extracted train the supernatant of HIV-1 in vitro cultures was amplified with NASBA using different primer sets for HIV-1 RNA (gag region) amplification. The HIV-1 viruses used in this example were of the subtypes A, B and C, which could be distinguished by mutations in the gag region that was amplified. The nucleic acid was extracted and purified using the "Boom" method (Boom R, Sol C J, Salimans M M, Jansen C L, Wertheirn-van Dillen P M, van der Noordaa J, 1990. Rapid and simple method for purification of nucleic acids. *J Clin Microbiol;* 28(3):495–503). After the extraction nucleic acid was eluted in 50 µl buffer (10 mM tris, pH7.5, 1 mM EDTA) or water and stored at −20° C. For amplification by NASBA 5 µl of this nucleic acid solution was used as input for the amplification reactions. The primers and molecular beacon probes (for reference see: Leone G, van Schijndel H, van Gemen B, Kramer F R, Schoen CD (1998) Molecular beacon probes combined with amplification by NASBA enable homogeneous, real-time detection of RNA, *Nucleic Acid Res May* 1;26(9):2150–2155) that were used in the experiment are described in table 1.

TABLE 1

Primers and probes used. (Sequence Listing incorporated by this reference.)

| | |
|---|---|
| Gap-p1: Primer P1 5' *AATTCTAATACGACTCACTATAGGG*TGCTATGTCACTCCCCTTGGTTCTCCTCA 3' | (SEQ. ID. NO. 1) |
| Gap-p2  Primer P2 5' AGTGGGGGGACATCAAGCAGCCATGCAAA3' | (SEQ. ID. NO. 2) |
| Type A-1 Probe 5' CGTACG TGGGACAGGTTACATCCAG CGTACG 3' | (SEQ. ID. NO. 3) |
| Type A-2 Probe 5' CGTACG TGGGACAGGTTACA<u>G</u>CCAG CGTACG 3' | (SEQ. ID. NO. 4) |
| Type B-1 Probe 5' CGTACG GAAGCTGCAGAATGGGATAGA CGTACG 3' | (SEQ. ID. NO. 5) |
| Type B-2 Probe 5' CGTACG GAAGCTGCAGAAT<u>G</u>AGATAGA CGTACG 3' | (SEQ. ID. NO. 6) |
| Type C-1 Probe 5' CGTACG CCATCAATGATGAGGCTGCA CGTACG 3' | (SEQ. ID. NO. 7) |
| Type C-2 Probe 5' CGTACG CCATCAATGA<u>A</u>GAGGCTGCA CGTACG 3' | (SEQ. ID. NO. 8) |

The T7 RNA promoter sequence that is part of the P1 primers is shown in italics. The stem sequences of the molecular beacons is given in bold. The purposely-mismatched nucleotides in the probes are underlined.

The molecular beacon probes that are used in this experiment are labeled with TET, ROX or FAM (the label) at the 5' ends for respectively type A, type B and type C. All probes are labeled with DABCYL (the quencher) at the 3' end. The NASBA reactions (Tris-HCl40 mM, pH=8.5, $MgCl_2$ 12 mM, KCl 70 mM, DTT 5 mM, dNTP's (each) 1 mM, rATP 2 mM, rUTP 2 mM, rCTP 2 mM, rGTP 1.5 mM, ITP 0.5 mM, EDTA 0.75 mM, DMSO 15% v/v, oligonucleotide P1 0.2 µM, oligonucleotide P2 0.2 µM, molecular beacon probe 0.2 µM and Sorbitol 0.375 M) were incubated at 65° C. for 5 minutes and subsequently at 41° C. for 5 minutes. Next, the enzyme mix was added, (BSA 2.1 mg, RNase H 0.01 units, T7 RNA Polymerase 37 units, AMV-RT 7.5 units) and after gentle mixing by tapping, the reactions were incubated at 41° C. in a fluorimeter (Cytofluor 4000, Perkin Elmer or ABI 7700, ABI) for 90 minutes with measurement of the fluorescent signal every minute. The results of the experiment are shown in FIG. 1.

From the results as shown in FIG. 1 it is clear that the introduction of a purposely made mismatch has resulted in increased specificity of the probes. (This is viewed by comparing the lower three panels with the upper three panels in FIG. 1). Specifically, FIG. 1 illustrates real time signal generation of NASBA reactions with different molecular beacon probes using different HIV-1 strains as input.

References

1. Morris T, Robertson B, Gallagher M. Rapid reverse transcription—PCR detection of hepatitis C virus RNA in serum by using the TaqMan fluorogenic detection system. J Clin Microbiol. 1996 December;34(12):2933–6.
2. Heid C A, Stevens J, Livak K J, Williams P M. Real time quantitative PCR. Genome Res. 1996 October; 6 (10):986–94.
3. Tyagi S, Kramer F R. Molecular beacons: probes that fluoresce upon hybridization. Nat Biotechnol. 1996 March; 14 (3):303–8.
4. Leone G, van Schijnciel H, van Gemen B, Kramer F R, Schoen C D. Molecular beacon probes combined with amplification by NASBA enable homogeneous, real-time detection of RNA. Nucleic Acids Res. 1998 May 1;26(9):2150–5
5. Holloway J W, Beghe B, Turner 5, Hinks L J, Day I N, Howell W M. Comparison of three methods for single nucleotide polymorphism typing for DNA bank studies: sequence-specific oligonucleotide probe hybridization, TaqMan liquid phase hybridization, and microplate array diagonal gel electrophoresis (MADGE). Hum Mutat. 1999;14(4):340–7.
6. Marras S A, Kramer F R, Tyagi S. Multiplex detection of single-nucleotide variations using molecular beacons. Genet Anal. 1999 Feb; 14(5–6):151–6.
7. Tyagi S, Bratu D P, Kramer F R. Multicolor molecular beacons for allele discrimination. Nat Biotechnol. 1998 January;16 (1):49–53.

What is claimed is:

1. A method for reducing background signals in a hybridization reaction of nucleic acids involving at least two homologous probes, wherein at least one of the two homologous probes is a non-linear probe, said method comprising:
introducing a mismatch with an intended target sequence in said non-linear probe; and
conducting a hybridization reaction using said at least two homologous probes, thereby reducing the background signals of the hybridization reaction.

2. The method according to claim 1 in which the homologous probes are designed to detect point mutations in at least one target sequence.

3. The method according to claim 1, wherein the mismatch in a nucleotide sequence comprises 1–3 nucleotides.

4. The method according to claim 1 wherein the at least one non-linear probe has a length from about 15 to about 50 nucleotides.

5. The method according to claim 1 wherein the at least one of the non-linear probes is provided with a detectable moiety.

6. The method according to claim 1, further comprising amplifying a nucleic acid sequence.

7. A method for reducing background signals in a hybridization reaction of nucleic acids involving at least two homologous target sequences, said method comprising:
providing for an intended mismatch between at least one of the two homologous target sequences and at least one non-linear probe; and
conducting a hybridization reaction using said at least two homologous target sequences, thereby reducing the background signals of the hybridization reaction.

8. The method according to claim 7, wherein at least two of said non-linear probes and/or two of said target sequences comprise an identical sequence except for a variation due to a point mutation or due to a mismatch in a nucleotide sequence.

9. The method according to claim 7, wherein the mismatch in a nucleotide sequence is located between 2 and 20 nucleotides upstream or downstream of a point mutation.

10. The method according to claim 7 in which the homologous probes are designed to detect point mutations in at least one target sequence.

11. The method according to claim 7, wherein the mismatch in a nucleotide sequence comprises 1–3 nucleotides.

12. The method according to claim 7 wherein the at least one non-linear probe has a length from about 15 to about 50 nucleotides.

13. The method according to claim 7 wherein the at least one of the non-linear probes is provided with a detectable moiety.

14. The method according to claim 7, further comprising amplifying a nucleic acid sequence.

15. A method of conducting a hybridization reaction comprising;

mixing a set of homologous probes for detecting at least one allelic variant of a nucleic acid, wherein at least one of said set of homologous probes is non-linear, said set of homologous probes comprising at least one sequence completely complementary to and specific for one of the allelic variants of said nucleic acid, except for a specific mismatch located upstream downstream or both upstream and downstream from the site of variation;

detecting variants of the nucleic acids; and using the set of homologous probes to conduct the hybridization reaction.

16. The method according to claim 15 wherein the nucleic acids are derived from a group of pathogens.

17. The method according to claim 16 wherein the nucleic acids represent a number of HIV-variants.

* * * * *

```
                            SEQUENCE LISTING

<160> NUMBER OF SEQ ID NOS:   8

<210> SEQ ID NO 1
<211> LENGTH: 54
<212> TYPE: DNA
<213> ORGANISM: Unknown
<220> FEATURE:
<223> OTHER INFORMATION: Gag-p1 -- Function : Primer P1

<400> SEQUENCE: 1
aattctaata cgactcacta tagggtgcta tgtcacttcc ccttggttct ctca          54

<210> SEQ ID NO 2
<211> LENGTH: 29
<212> TYPE: DNA
<213> ORGANISM: Unknown
<220> FEATURE:
<223> OTHER INFORMATION: Gag-p2  -- Function : Primer P2

<400> SEQUENCE: 2
agtgggggga catcaagcag ccatgcaaa                                      29

<210> SEQ ID NO 3
<211> LENGTH: 31
<212> TYPE: DNA
<213> ORGANISM: Unknown
<220> FEATURE:
<223> OTHER INFORMATION: Type A-1 -- Function : Probe

<400> SEQUENCE: 3
cgtacgtggg acaggttaca tccagcgtac g                                   31

<210> SEQ ID NO 4
<211> LENGTH: 31
<212> TYPE: DNA
<213> ORGANISM: Unknown
<220> FEATURE:
<223> OTHER INFORMATION: Type A-2 -- Function : Probe

<400> SEQUENCE: 4
```

-continued

```
cgtacgtggg acaggttaca gccagcgtac g                                    31

<210> SEQ ID NO 5
<211> LENGTH: 33
<212> TYPE: DNA
<213> ORGANISM: Unknown
<220> FEATURE:
<223> OTHER INFORMATION: Type B-1 -- Function : Probe

<400> SEQUENCE: 5
cgtacggaag ctgcagaatg ggatagacgt acg                                  33

<210> SEQ ID NO 6
<211> LENGTH: 33
<212> TYPE: DNA
<213> ORGANISM: Unknown
<220> FEATURE:
<223> OTHER INFORMATION: Type B-2 -- Function : Probe

<400> SEQUENCE: 6
cgtacggaag ctgcagaatg agatagacgt acg                                  33

<210> SEQ ID NO 7
<211> LENGTH: 32
<212> TYPE: DNA
<213> ORGANISM: Unknown
<220> FEATURE:
<223> OTHER INFORMATION: Type C-1 -- Function : Probe

<400> SEQUENCE: 7
cgtacgccat caatgatgag gctgcacgta cg                                   32

<210> SEQ ID NO 8
<211> LENGTH: 32
<212> TYPE: DNA
<213> ORGANISM: Unknown
<220> FEATURE:
<223> OTHER INFORMATION: Type C-2 -- Function : Probe

<400> SEQUENCE: 8
cgtacgccat caatgaagag gctgcacgta cg                                   32
```